United States Patent [19]

Hudek, deceased et al.

[11] 4,374,524
[45] Feb. 22, 1983

[54] ELECTROMEDICAL APPARATUS FOR INTERFERENCE CURRENT TREATMENT

[75] Inventors: Karl Hudek, deceased, late of Erlangen, Fed. Rep. of Germany, by Amanda Hudek, Gerd Hudek, Kurt Hudek, heirs; Bernd Kusserow, Erlangen, Fed. Rep. of Germany

[73] Assignee: Siemens Aktiengesellschaft, Berlin & Munich, Fed. Rep. of Germany

[21] Appl. No.: 174,853

[22] Filed: Aug. 4, 1980

[30] Foreign Application Priority Data

Aug. 3, 1979 [DE] Fed. Rep. of Germany ....... 2931638

[51] Int. Cl.³ .............................................. A61N 1/36
[52] U.S. Cl. ................................................ 128/420 A
[58] Field of Search .............. 128/420 A, 420 R, 421, 128/422

[56] References Cited

U.S. PATENT DOCUMENTS

| | | | |
|---|---|---|---|
| 3,895,639 | 7/1975 | Rodler | 128/420 A X |
| 3,958,577 | 5/1976 | Rodler | 128/420 A |
| 4,153,061 | 5/1979 | Nemec | 128/420 A |
| 4,280,504 | 7/1981 | Rodler | 128/420 A |

FOREIGN PATENT DOCUMENTS 2159437 4/1973 Fed. Rep. of Germany ... 128/420 A

*Primary Examiner*—Lee S. Cohen
*Attorney, Agent, or Firm*—Hill, Van Santen, Steadman, Chiara & Simpson

[57] ABSTRACT

In an exemplary embodiment, the simultaneous intensity control of the individual current circuits is to be effected while avoiding undesired intensity deviations in the current circuits such as occur because of nonuniformity of multiple potentiometers, for example. Expediently, the signal frequencies are digitally generated. According to the disclosure, in every output current circuit a transistor is connected-in, which is switched between a conducting and a nonconducting condition so that the collector output exhibits either a zero value or an operating voltage value, all switching transistors being activated on the collector side via a common control element from a single voltage source. In the through-connected state, the collector voltages of the switching transistors have the same value, respectively, which can be synchronously varied in dependence upon the setting of common control element.

8 Claims, 3 Drawing Figures

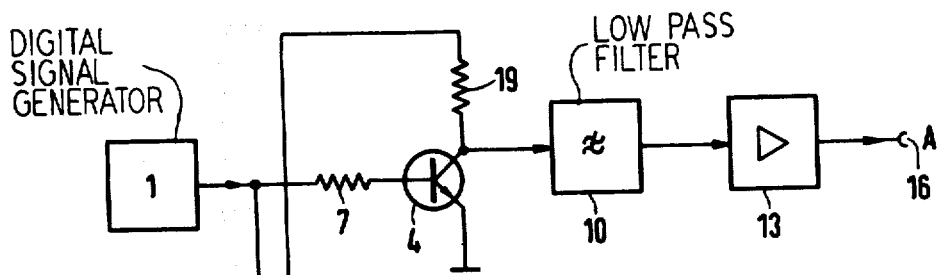
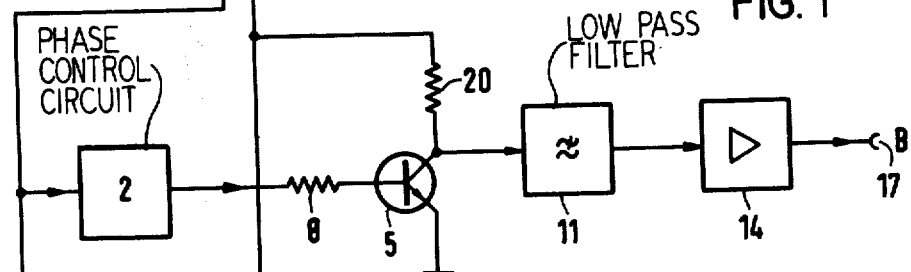
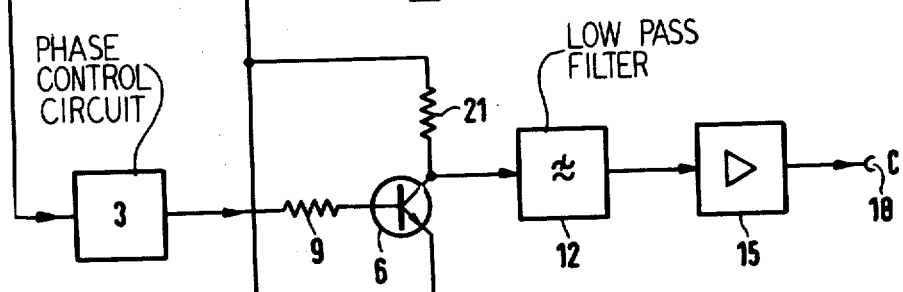
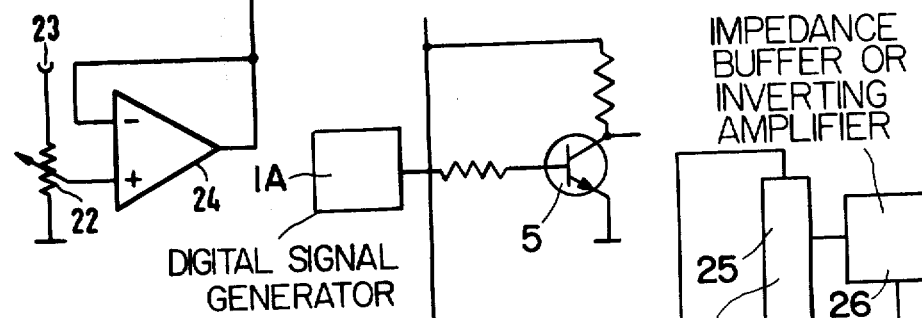
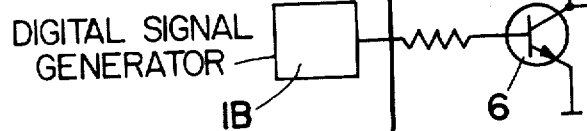
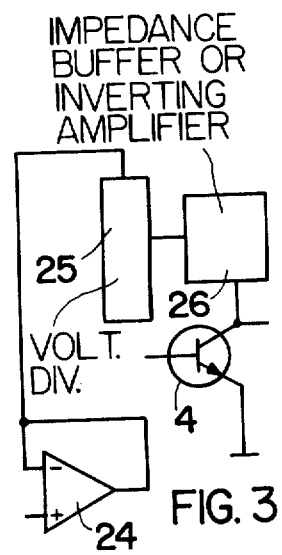
FIG. 1
FIG. 2
FIG. 3

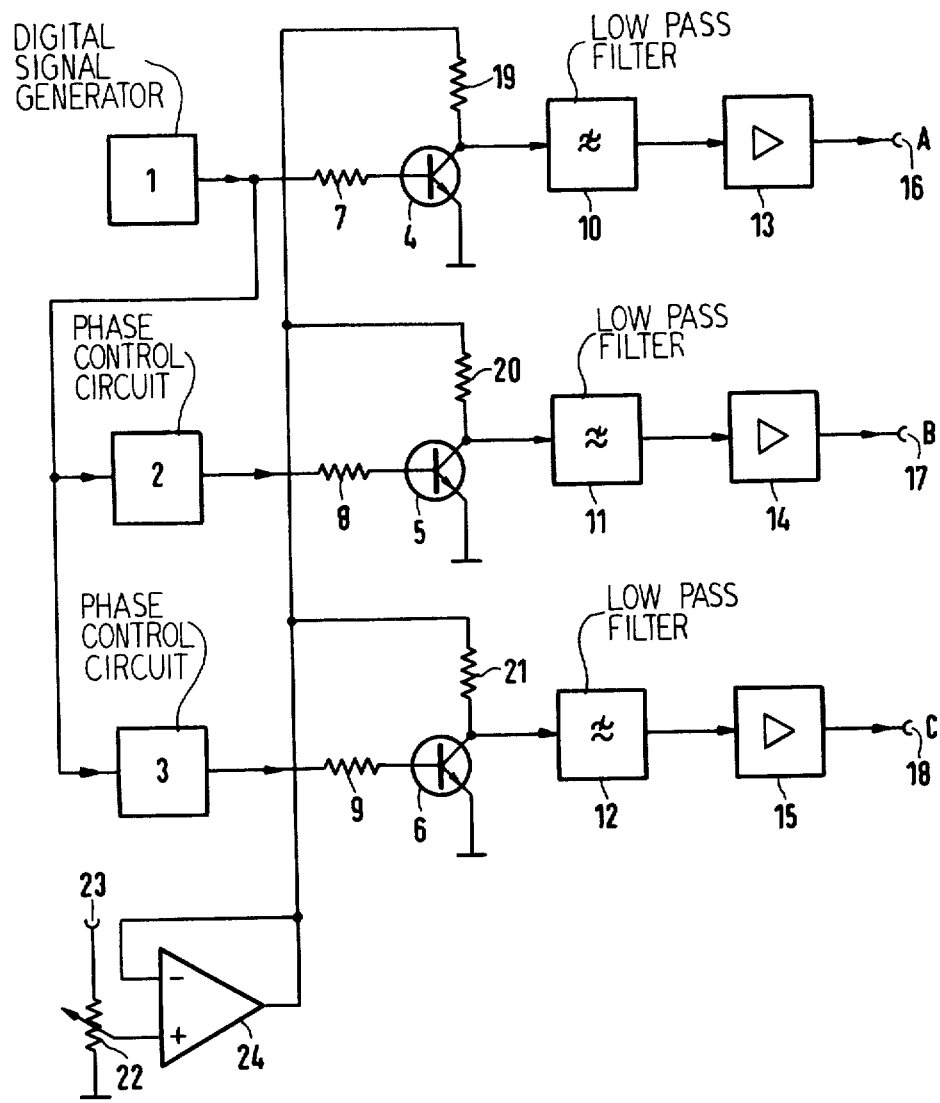

ELECTROMEDICAL APPARATUS FOR INTERFERENCE CURRENT TREATMENT

BACKGROUND OF THE INVENTION

The invention relates to an electromedical apparatus for interference current treatment comprising at least two current circuits, wherein the current circuits are activated either by a generator for the purpose of digital generation of signal frequencies and are interconnected via phase control circuits, or said current circuits are activated by separate generators for the purpose of generating signal frequencies of small deviation (of low frequency differences).

In the case of current stimulation apparatus according to the interference principle, an intensity control is to be possible simultaneously and uniformly in the individual current circuits; this means that no noticeable synchronization faults can be permitted to occur between the channels of the current stimulation apparatus.

Up to the present time, the current intensity of the current circuits was controlled by multicircuit interference apparatus comprising multiple potentiometers. Basically, simultaneously several potentiometers are activated with a rotary knob by the operator. The synchronization error of conventional multiple potentiometers, however, lies approximately on the order of magnitude of ±3 db. As a consequence of this, undesired shifts in the intensity progression of the individual channels can effectively already result. The same accordingly applies when the intensity progression of the current circuits is controlled by the steepness (or slope) of the input/output transfer characteristics of field effect transistors. Since the steepness of the transfer characteristic and the so-called "pinch-off-voltages" of such components can vary greatly, it is necessary, in this instance, to reckon with a considerable outlay of adjustment elements and adjustment time.

SUMMARY OF THE INVENTION

Accordingly, the object underlying the invention resides in producing an electromedical apparatus for inteference current treatment in which, with the least possible technical outlay, the intensity control of the individual current circuits is possible in an entirely uniform fashion.

In accordance with the invention, the object is achieved in the case of an apparatus of the type initially cited in that, in every output current circuit, a transistor is connected whose collector voltage exhibits, during switching operation at the signal frequency rate, either zero value or operating voltage value, all switching transistors being activated at the collector side via a common control element from a single voltage source, so that the magnitude of the output signals of the switching transistors of all output current circuits synchronously varies in dependence upon the position of the common control element.

Since the signal frequencies are digitally generated; i.e., they are present in the form of square wave voltages, the transistors can be employed as switches which are switched to the conductive stage by the square wave voltage of the generators for the various current circuits. The output square wave voltage, which is available at the transistors on the collector side, is here a function of the position of the common control element, which is identical for all current circuits. Preferably the common control element is a potentiometer which is connected at its output to an operational amplifier, the amplifier being operated with a feedback coupling, so that, through the low-resistance output, no cross talk can take place in the parallel-connected channels of the individual transistors. From the digital signal values; i.e., the output square wave voltages, sinusoidal voltages can be correspondingly generated through low-pass filters which are connected at the output side with the collector paths. These sinusoidal voltages are post-amplified by identical amplifiers, so that the voltages for producing the desired interference currents in the patient are available at the output electrodes.

Further details and advantages of the invention are apparent from the following figure description of an exemplary embodiment on the basis of the accompanying drawing sheet in conjunction with additional subclaims; and other objects, features and advantages will be apparent from this detailed disclosure and from the appended claims.

BRIEF DESCRIPTION OF THE DRAWING

FIG. 1 illustrates in a circuit diagram an interference current apparatus with simultaneous, identical intensity control of the current circuits;

FIG. 2 illustrates a modification of FIG. 1 wherein separate digital signal generators are provided; and FIG. 3 illustrates a modification of FIG. 1 wherein a voltage divider and impedance converter means are interposed between the common control circuit and the respective switching transistors.

DETAILED DESCRIPTION

In FIG. 1, reference character A denotes the channel of a first current circuit; B, the channel of a second current circuit; and C, the channel of a third current circuit, the outputs of which can be applied via electrodes to corresponding locations of the patient's body for the purpose of developing interference currents in the interior of the patient. Reference numeral 1 characterizes a signal generator for the purpose of generating signal frequencies approximately in the medium frequency range; for example, between 1000 and 100,000 Hz. The signal generator 1 directly activates the current circuit A. Connected in parallel with the generator 1 are phase control circuits 2 and 3 (so-called phase-locked-loops), with which rhythmic phase shifts in the current circuits B and C can be adjusted. Alternatively thereto, separate generators such as 1A, 1B, FIG. 2, for every current circuit can be employed which generate the frequencies of low frequency differences suitable for interference treatment. In the three current circuits, one transistor 4, 5 and 6 each is arranged which operate in the switching mode. Specifically, npn-transistors in common emitter connection are illustrated, whereby the base of each of the respective transistors 4 through 6 is connected with a respective one of resistances 7 through 9. The emitter path of each of the transistors 4 through 6 is connected to ground potential. The transistors 4 through 6, on the collector-side, have their outputs connected with respective low-pass filters 10 through 12, and respective identical amplifiers 13 through 15, by which current outputs 16 through 18 of the current circuits A through C are activated.

The collector outputs of the respective transistors 4, 5 and 6 are in each instance connected via a respective resistance 19 through 21 to a common control line. This control line is connected via a potentiometer 22 as common intensity control element to a voltage source 23. An operational amplifier 24 with a feedback coupling to its inverting input, as impedance converter, is connected to the potentiometer 22 at its direct input, so that the output to the common collector-side control line of the transistors 4 through 6 is of a low-resistance in comparison to the resistance values of resistances 19, 20 and 21. A mutual influencing of the channels of the individual current circuits is thereby prevented.

The circuit thus described has the following function: from the generator 1, square wave signals with cyclically varying phase position are connected directly or via the phase-locked-loops 2 and 3, to the signal lines for the individual channels A through C. The transistors 4 through 6 are in each instance driven to saturation by the input signals, so that they operate, in dependence upon the digitally present signals, in the switching mode between full conducting and cut off with the specified frequency. The collector voltages of the transistors 4 through 6 are then either zero or operating voltage. The operating voltage of the transistors 4 through 6 is synchronously adjusted for all transistors to the desired value by means of the single potentiometer 22. Through the operational amplifier 24 with the feedback connection to its inverting input, cross-talk between the individual channels via the transistors 4 through 6 is prevented, so that actually in each instance there is present, at the collector side, the same square wave voltage which is a function of the setting of the common potentiometer 22. These square wave voltages are converted via the low pass filters 10 through 12 to sinusoidal voltages and the sinusoidal voltages are amplified in the amplifiers 13 through 15. The outputs 16 through 18 of the channels A, B, C, can be applied via electrodes directly to the patient's body in which the desired interference currents develop.

In another exemplary embodiment, the transistors of the individual current circuits are additionally connected, on the collector side, with a voltage divider such as 25, FIG. 3. The intensity of individual current circuits can thereby be varied, while the synchronous relative change (or variation), in dependence upon the setting of the control unt 22-24, remains present. Expediently, an impedance converter (or buffer) such as 26; here is connected with each output of the voltage divider 25, the respective taps of the voltage divider supplying the respective operating voltages to the respective collectors of the transistors via the respective impedance buffers. It is also possible, through connection of an inverting amplifier between one or more of the taps of the voltage divider and the respective collector or collectors, to create such a control in which the intensities in the individual current circuits vary in a definedly opposed fashion.

It will be apparent that many modifications and variations may be effected without departing from the scope of the novel concepts and teachings of the present invention. We claim as our invention:

1. Electromedical apparatus for interference current treatment comprising at least two current circuits having current circuit output means adapted to be coupled to a patient for the purpose of interference current treatment, generator means activating the current circuits with signal frequencies of timing characteristics for effecting interference current treatment via said current circuit output means, each current circuit having a switching transistor (4, 5, 6) connected with said generator means, the transistors (4, 5, 6) having respective collector circuits for supplying collector voltages to the switching transistors, the signal frequencies from the generator means serving to operate the transistors in a switching mode such that the collector voltage of each transistor successively switches between a zero value and an operating voltage value, common control means connected with all of said collector circuits and comprising a single voltage source (23) and a common control circuit (22, 24) having an adjustable common control element means (22) for controlling the activating voltage supplied to each collector circuit so that all switching transistors (4, 5, 6) are activated on the collector side from said single voltage source (23) via said common control circuit (22, 24), and so that the magnitudes of the collector output signals of all of the switching transistors (4, 5, 6) are synchronously adjustable in dependence upon the setting of the common control element means (22), the common control element means being a potentiometer (22) connected with said single voltage source (23), said common control circuit further comprising an operational amplifier (24) having feedback circuit means providing an output-to-input current path and thereby providing a low-resistance output from said operational amplifier connected with all of said collector circuits, said operational amplifier having an amplifier input means connected with said potentiometer (22), said amplifier input means being connected with said single voltage source (23) under the control of said potentiometer (22), said current circuits further having low pass filters (10, 11, 12) having filter inputs connected with the collectors of said transistors (4, 5, 6) and having filter outputs connected with said current circuit output means for supplying sinusoidal signals in accordance with the frequency and phase of the signal frequencies.

2. Electromedical apparatus according to claim 1, characterized in said current circuits further comprising identical amplifiers (13, 14, 15) connected between the outputs of said low pass filters (10, 11, 12) and the current circuit output means.

3. Electromedical apparatus according to claim 1, with said generator means comprising a digital signal generator and phase-locked loop circuit means having an input connected to said digital signal generator and having an output connected with an input electrode of one of said transistors, said generator and circuit means supplying respective digital signals for driving the transistors into saturation in accordance with the frequency and phase of the respective digital signals.

4. Electromedical apparatus according to claim 1, with said generator means comprising a common digital signal generator and respective phase-locked loop circuits connected with the inputs of said transistors, and being operable for supplying digital signals with predetermined different phases to the inputs of said transistors so that the transistors are all switched between a conducting and a nonconducting state at the frequency of said common digital signal generator but with phase characteristics for effecting interference current treatment.

5. Electromedical apparatus according to claim 1, characterized in that said current circuits have voltage divider means with input means connected with said common control circuit and outputs connected to the switching transistors (4, 5, 6) on the collector side, so that the magnitudes of the operating voltage values of the individual switching transistors (4, 5, 6) are adjustable in a defined ratio in dependence upon the setting of the common control element means (22).

6. Electromedical apparatus according to claim 5, characterized in that said current circuits have impedance converter means connected between the outputs of the voltage divider means and said collector circuits.

7. Electromedical apparatus according to claim 5, characterized in that at least one of said current circuits has an inverting amplifier connected between an output of the voltage divider means and the one collector circuit.

8. Electromedical apparatus according to claim 1, with said generator means comprising separate digital signal generators generating signal frequencies of low frequency difference and connected with the input electrodes of the respective switching transistors for cyclically driving the switching transistors into saturation at the respective signal frequencies.

* * * * *